(12) United States Patent
Huang

(10) Patent No.: US 7,752,885 B2
(45) Date of Patent: Jul. 13, 2010

(54) GAS ANALYSIS SYSTEM AND METHOD

(75) Inventor: Yufeng Huang, North Chelmsford, MA (US)

(73) Assignee: General Electric Company, Schenectady, NY (US)

( * ) Notice: Subject to any disclaimer, the term of this patent is extended or adjusted under 35 U.S.C. 154(b) by 744 days.

(21) Appl. No.: 11/567,763

(22) Filed: Dec. 7, 2006

(65) Prior Publication Data

US 2008/0134751 A1    Jun. 12, 2008

(51) Int. Cl.
*G01N 29/02* (2006.01)
*G01N 7/00* (2006.01)

(52) U.S. Cl. ............... 73/23.2; 73/23.21; 73/23.25; 73/23.27; 73/23.28; 73/30.01; 73/30.02; 73/30.03; 73/30.04; 73/31.04

(58) Field of Classification Search .......... 73/23.2, 73/23.21, 23.25, 23.27, 23.28, 30.01, 30.02, 73/30.03, 30.04, 31.04
See application file for complete search history.

(56) References Cited

U.S. PATENT DOCUMENTS

| | | | |
|---|---|---|---|
| 4,856,321 A | 8/1989 | Smalling et al. | |
| 6,216,091 B1 | 4/2001 | Hammond | |
| 6,850,847 B2 | 2/2005 | Morrow et al. | |
| 2004/0158411 A1 | 8/2004 | Morrow et al. | |
| 2005/0143937 A1 | 6/2005 | Morrow et al. | |

FOREIGN PATENT DOCUMENTS

WO      WO00/19176 A     4/2000
WO      WO01/79830 A    10/2001

OTHER PUBLICATIONS

Lueptow R M et al: "Acoustic sensor for determining combustion properties of natural gas" Measurement Science and Technology Institute of Physics Publishing, Bristol GB, vol. 5, No. 11, Nov. 1, 1994 pp. 1375-1384.

*Primary Examiner*—Daniel S Larkin
(74) *Attorney, Agent, or Firm*—Global Patent Operation; Mark A. Conklin

(57) ABSTRACT

A gas specimen mixture analysis system includes at least one sensor for measuring the concentrations of inert components in the gas specimen mixture, a pressure sensor for measuring the pressure of the gas specimen mixture, and a temperature sensor for measuring the temperature of the gas specimen mixture. A subsystem measures the speed of sound in the gas specimen mixture, and a processing subsystem, responsive to the at least one inert component sensor, the pressure sensor, the temperature sensor, and the subsystem for measuring the speed of sound, is configured to generate a number of sample gas mixtures with varying percentages of hydrocarbon gases, each including the measured inert component concentrations. The processing subsystem is also configured to calculate, for each generated sample gas mixture, the speed of sound therein based on the measured pressure and temperature and the particular percentages of hydrocarbon gases therein, and iteratively compare the measured speed of sound with the calculated speed of sound in different sample gas mixtures until convergence for a particular sample gas mixture. The processing subsystem is further configured to calculate the molecular weight of the particular sample gas mixture and set the molecular weight of the gas specimen mixture to the calculated molecular weight.

24 Claims, 11 Drawing Sheets

GAS ANALYSIS SYSTEM AND METHOD

FIELD OF THE INVENTION

The subject invention relates to analysis of a gas, such as natural gas which is principally made up of hydrocarbon gases, to determine various properties of the gas.

BACKGROUND OF THE INVENTION

Various systems and methods exist for determining properties of multi-component gases. The gas' heating value, energy flow, mass flow and the like are typical properties of interest. Before a natural gas transmission pipeline company transfers or sells natural gas to distribution companies, the energy content in the natural gas has to be determined within a certain accuracy. Also, the energy measurement is preferred to be on-line during the transfer and in real time. Additionally, a fast and accurate determination of energy in the fuel line of a natural gas turbine would provide for optimal combustion.

Traditionally, energy content in natural gas is calculated from a complete gas analysis through gas chromatography. Gas chromatography is mostly an "off-line" analysis with a slow response time. Its operational cost is high due to required consumables and frequent calibrations.

Also, some known systems for determining gas properties without a complete gas analysis typically make determinations based on limited or fixed, not dynamic, correlations between various components and properties of the gas. U.S. Pat. Nos. 6,850,847 and 6,216,091, which are each incorporated herein by reference, are some examples of known methods. See, e.g. www.elster-instromet.com/downloads/ELS_G-M_EnSonic_DS_UK_ol_l.pdf, which is incorporated herein by reference.

The challenge is to determine a gas' energy, such as heating value and other properties, more accurately, in real time, and at low cost.

SUMMARY OF THE INVENTION

The present invention provides for more accurate measurement of energy content in natural gas, for example, among other properties. The measurement can be on-line, with fast response time, at a lower cost, and can be used in custody transfer applications and/or for energy content measurement in a fuel line for a gas turbine, among other uses. Embodiments of this invention provide a cost-effective, less complex, more accurate method and system for determining the molecular weight of a gas to be measured, thus providing a more accurate determination of gas properties such as heating value, and energy flow and mass flow.

In the embodiments of this invention, the applicants' method and system includes a determination of the molecular weight of a multi-component gas to be measured as well as various properties of the gas, utilizing the speed of sound of the gas and its inert components content, such as its nitrogen and carbon dioxide content, when the gas is at any pressure and temperature. These determinations can be made dynamically, and the invention provides improved accuracy with less complexity and may be incorporated in various conventional field instruments.

The invention embodiments, however, need not achieve all these objectives and results and the claims hereof should not be limited to structures or methods capable of achieving these objectives and results.

This invention features a gas specimen mixture analysis system including at least one sensor for measuring the concentrations of inert components in the gas specimen mixture, a pressure sensor for measuring the pressure of the gas specimen mixture, and a temperature sensor for measuring the temperature of the gas specimen mixture. The system also includes a subsystem for measuring the speed of sound in the gas specimen mixture, and a processing subsystem, responsive to the at least one inert component sensor, the pressure sensor, the temperature sensor, and the subsystem for measuring the speed of sound. The processing subsystem is configured to generate a number of sample gas mixtures with varying percentages of hydrocarbon gases but each including the measured inert component concentrations, calculate, for each generated sample gas mixture, the speed of sound therein based on the measured pressure and temperature and the particular percentages of hydrocarbon gases therein, iteratively compare the measured speed of sound with the calculated speed of sound in different sample gas mixtures until convergence for a particular sample gas mixture, calculate the molecular weight of the particular sample gas mixture, and set the molecular weight of the gas specimen mixture to the calculated molecular weight. In one embodiment, the at least one inert component sensor includes a nitrogen sensor for measuring the nitrogen gas concentration in the gas specimen mixture and a carbon dioxide sensor for measuring the concentration of carbon dioxide in the gas specimen mixture. Convergence may be set to equality or to a difference between the measured speed of sound and a calculated speed of sound less than or equal to 0.001%. The subsystem for measuring the speed of sound typically includes at least one ultrasonic transducer. The processing subsystem may be further configured to generate an antecedent sample gas mixture including hydrocarbon gases each at percentages which fall within predetermined ranges, and to generate a subsequent sample gas mixture with at least one hydrocarbon gas at a different percentage than in the antecedent sample gas mixture but still constrained to fall within the predetermined range. The processing subsystem, when the calculated speed of sound in an antecedent sample gas mixture is greater than the measured speed of sound in the gas specimen mixture, may be configured to generate a subsequent sample gas mixture with percentages of lighter hydrocarbon gases decreased from the percentages of lighter hydrocarbon gases in the antecedent sample gas mixture, and/or to generate a subsequent sample gas mixture with percentages of heavier hydrocarbon gases increased from the percentages of the heavier hydrocarbon gases in the antecedent sample gas mixture. The processing subsystem, when the calculated speed of sound in an antecedent sample gas mixture is less than the measured speed of sound in the gas specimen mixture, may be configured to generate a subsequent sample gas mixture with percentages of lighter hydrocarbon gases increased from the percentages of lighter hydrocarbon gases in the antecedent sample gas mixture, and/or to generate a subsequent sample gas mixture with percentages of heavier hydrocarbon gases decreased from the percentages of heavier hydrocarbon gases in the antecedent sample gas mixture.

In a further embodiment the processing subsystem is configured to determine the heating value of the gas specimen mixture by the steps including converting the molecular weight of the gas specimen mixture to a pure hydrocarbon molecular weight, generating a plurality of sample gas mixtures each having pure hydrocarbon molecular weights, and plotting a correlation curve based on the pure hydrocarbon molecular weights for the plurality of sample gas mixtures and mass-based heating values of the pure hydrocarbon molecular weights for the plurality of sample gas mixtures, interpolating the mass-based heating value of the pure hydrocarbon molecular weight for the gas specimen mixture from the correlation curve, determining the mass-based heating value of the gas specimen mixture, and calculating the volume-based heating value of the gas specimen mixture using the mass-based heating value of the gas specimen mixture and density of the gas specimen mixture. The step of converting the molecular weight of the gas specimen mixture to a pure hydrocarbon molecular weight includes replacing the measured inert component concentrations with proportionately equivalent concentrations of hydrocarbon gases, and determining the mass-based heating value of the gas specimen mixture includes replacing the proportionately equivalent concentrations of hydrocarbon gases with the measured inert component concentrations. In one variation, calculating the volume-based heating value of the gas specimen mixture includes multiplying the mass-based heating value of the gas specimen times the density of the gas specimen mixture. The density of the gas specimen mixture is a standard density for the gas specimen mixture based on predetermined temperature and pressure values, and the calculated heating value is the volume-based heating value of the gas specimen mixture at standard temperature and pressure. The density of the gas specimen mixture is the real density of the gas specimen mixture based on the measured pressure and temperature, and the calculated heating value is the volume-based heating value of the gas specimen mixture at the measured temperature and pressure. In a further embodiment the processing subsystem is configured to calculate the energy flow of the gas specimen mixture from the volume-based heating value of the gas specimen mixture at the measured temperature and pressure and volumetric flow rate of the gas specimen mixture. The volumetric flow rate of the gas specimen mixture may be measured by a flow meter. Calculating the energy flow of the gas specimen mixture includes multiplying the volume-based heating value of the gas specimen mixture at the measured temperature and pressure times the volumetric flow rate.

In another embodiment, the processing subsystem includes determining the mass flow rate of the gas specimen mixture by the steps including measuring the volumetric flow rate of the gas specimen mixture, determining the density of the gas specimen mixture, and calculating the mass flow of the gas specimen mixture based on the density and the volumetric flow rate. The volumetric flow rate may be measured by a flow meter. In one configuration, the step of determining the density includes the steps including measuring the temperature and pressure of the gas specimen mixture, calculating the density of the particular sample gas mixture from the measured temperature and pressure, and setting the density of the gas specimen mixture to the calculated density. In another configuration, determining the density includes the steps including calculating the specific gravity of the gas specimen mixture from the molecular weight of the gas specimen mixture, and converting the calculated specific gravity to density using the measured inert component concentrations. Calculating the mass flow rate includes multiplying the density times the volumetric flow rate.

This invention also features a system of analyzing a gas specimen mixture, the system including sensors for measuring the nitrogen gas and carbon dioxide concentrations of the gas specimen mixture, sensors for measuring the pressure and temperature of the gas specimen mixture, and a processing subsystem. The processing subsystem is configured to generate an antecedent sample gas mixture including hydrocarbon gases each at a percentage which fall within the predetermined range, calculate the speed of sound in the antecedent sample gas mixture based on the measured pressure and temperature, measure the speed of sound in the gas specimen mixture, and compare the measured speed of sound with the calculated speed of sound and, based on the difference therebetween, generate a subsequent sample gas mixture with at least one hydrocarbon gas at a different percentage than in the antecedent sample gas mixture but still constrained to fall within the predetermined range. The processing subsystem may be further configured to iteratively compare the measured speed of sound with the calculated speed of sound in different generated sample gas mixtures until there is convergence for a particular sample gas mixture, and to calculate the molecular weight of the particular sample gas mixture and set the molecular weight of the gas specimen mixture to the calculated molecular weight. When the calculated speed of sound in an antecedent sample gas mixture is greater than the measured speed of sound in the gas specimen mixture, the processing subsystem may be configured to generate a subsequent sample gas mixture with percentages of lighter hydrocarbon gases decreased from the percentages of lighter hydrocarbon gases in the antecedent sample gas mixture, and/or when the calculated speed of sound in a sample gas mixture is greater than the measured speed of sound in the gas specimen mixture, the processing subsystem may be configured to generate a subsequent sample gas mixture with percentages of heavier hydrocarbon gases increased from the percentages of the heavier hydrocarbon gases in the antecedent sample gas mixture. When the calculated speed of sound in an antecedent sample gas mixture is less than the measured speed of sound in the gas specimen mixture, the processing subsystem may be configured to generate a subsequent sample gas mixture with percentages of lighter hydrocarbon gases increased from the percentages of lighter hydrocarbon gases in the antecedent sample gas mixture, and/or when the calculated speed of sound in an antecedent sample gas mixture is less than the measured speed of sound in the gas specimen mixture, the processing subsystem may be configured to generate a subsequent sample gas mixture with percentages of heavier hydrocarbon gases decreased from the percentages of heavier hydrocarbon gases in the antecedent sample gas mixture.

In one embodiment, the processing subsystem is further configured to determine the heating value of the gas specimen mixture by the steps including converting the molecular weight of the gas specimen mixture to a pure hydrocarbon molecular weight, generating a plurality of sample gas mixtures each having pure hydrocarbon molecular weights, plotting a correlation curve based on the pure hydrocarbon molecular weights for the plurality of sample gas mixtures and mass-based heating values of the pure hydrocarbon molecular weights for the plurality of sample gas mixtures, interpolating the mass-based heating value of the pure hydrocarbon molecular weight for the gas specimen mixture from the correlation curve, determining the mass-based heating value of the gas specimen mixture, and calculating the volume-based heating value of the gas specimen mixture using the mass-based heating value of the gas specimen mixture and density of the gas specimen mixture. In one example, converting the molecular weight of the gas specimen mixture to a pure hydrocarbon molecular weight includes replacing the measured nitrogen gas and carbon dioxide concentrations with proportionately equivalent concentrations of hydrocarbon gases, and determining the mass-based heating value of the gas specimen mixture includes replacing the proportionately equivalent concentrations of hydrocarbon gases with the measured nitrogen gas and carbon dioxide concentrations. Calculating the volume-based heating value of the gas specimen mixture includes multiplying the mass-based heating value of the gas specimen times the density of the gas specimen mixture. The density of the gas specimen mixture may be a standard density for the gas specimen mixture based on predetermined temperature and pressure values, and the calculated heating value is the volume-based heating value of the gas specimen mixture at standard temperature and pressure. Alternatively, the density of the gas specimen mixture may be the real density of the gas specimen mixture based on the measured pressure and temperature, and the calculated heating value is the volume-based heating value of the gas specimen mixture at the measured temperature and pressure.

In another embodiment, the processing subsystem is further configured to calculate the energy flow of the gas specimen mixture from the volume-based heating value of the gas specimen mixture at the measured temperature and pressure and volumetric flow rate of the gas specimen mixture. The volumetric flow rate of the gas specimen mixture may be measured by a flow meter, and calculating the energy flow of the gas specimen mixture may include multiplying the volume-based heating value of the gas specimen mixture at the measured temperature and pressure times the volumetric flow rate.

In a further embodiment, the system in which the processing subsystem is further configured to determine the mass flow rate of the gas specimen mixture by the steps including measuring the volumetric flow rate of the gas specimen mixture, determining the density of the gas specimen mixture, and calculating the mass flow of the gas specimen mixture based on the density and the volumetric flow rate. The volumetric flow rate may be measured by a flow meter. The step of determining the density may include the steps including measuring the temperature and pressure of the gas specimen mixture, calculating the density of the particular sample gas mixture from the measured temperature and pressure, and setting the density of the gas specimen mixture to the calculated density. Alternatively, determining the density may include the steps of calculating the specific gravity of the gas specimen mixture from the molecular weight of the gas specimen mixture, and converting the calculated specific gravity to density using the measured nitrogen gas and carbon dioxide concentrations. Calculating the mass flow rate includes multiplying the density times the volumetric flow rate.

This invention further features a gas specimen mixture analysis system including at least one sensor for measuring the concentration of inert components in the gas specimen mixture, a pressure sensor for measuring the pressure of the gas specimen mixture, a temperature sensor for measuring the temperature of the gas specimen mixture, a subsystem for measuring the speed of sound in the gas specimen mixture, and a processing subsystem. The processing subsystem is responsive to the at least one inert component sensor, the pressure sensor, the temperature sensor, and the subsystem for measuring the speed of sound, and configured to generate a number of sample gas mixtures with varying percentages of hydrocarbon gases but each including the measured inert component concentrations, calculate, for each generated sample gas mixture, the speed of sound therein and molecular weight based on the measured pressure and temperature and the particular percentages of hydrocarbon gases therein, generate an interrelationship between the calculated speed of sound and molecular weight for each generated sample gas mixture, and set the molecular weight of the gas specimen mixture based on the interrelationship using the measured speed of sound in the gas specimen mixture. The at least one inert component sensor may include a nitrogen sensor for measuring the nitrogen gas concentration in the gas specimen mixture and a carbon dioxide sensor for measuring the concentration of carbon dioxide in the gas specimen mixture. The processing subsystem may also be configured to plot a correlation curve based on the calculated speed of sound and molecular weight for each generated sample gas mixture, and to set the molecular weight of the gas specimen mixture by interpolating from the correlation curve using the measured speed of sound in the gas specimen mixture. In another variation, the processing subsystem may be configured to formulate an equation based on the calculated speed of sound and molecular weight for each generated sample gas mixture, and to set the molecular weight of the gas specimen mixture by solving the equation using the measured speed of sound in the gas specimen mixture. The hydrocarbon gases in the sample gas mixtures may be methane, ethane, propane, butane, pentane, hexane, heptane, octane, nonane, and/or decane. The subsystem for measuring the speed of sound typically includes at least one ultrasonic transducer.

In one embodiment, the processing subsystem is configured to determine the heating value of the gas specimen mixture by the steps including converting the molecular weight of the gas specimen mixture to a pure hydrocarbon molecular weight, generating a plurality of sample gas mixtures each having pure hydrocarbon molecular weights, and plotting a correlation curve based on the pure hydrocarbon molecular weights for the plurality of sample gas mixtures and mass-based heating values of the pure hydrocarbon molecular weights for the plurality of sample gas mixtures, interpolating the mass-based heating value of the pure hydrocarbon molecular weight for the gas specimen mixture from the correlation curve, determining the mass-based heating value of the gas specimen mixture, and calculating the volume-based heating value of the gas specimen mixture using the mass-based heating value of the gas specimen mixture and density of the gas specimen mixture. In one variation, converting the molecular weight of the gas specimen mixture to a pure hydrocarbon molecular weight includes replacing the measured inert component concentrations with proportionately equivalent concentrations of hydrocarbon gases, and determining the mass-based heating value of the gas specimen mixture includes replacing the proportionately equivalent concentrations of hydrocarbon gases with the measured inert component concentrations. In one example, calculating the volume-based heating value of the gas specimen mixture includes multiplying the mass-based heating value of the gas specimen times the density of the gas specimen mixture. The density of the gas specimen mixture may be a standard density for the gas specimen mixture based on predetermined temperature and pressure values, and the calculated heating value is the volume-based heating value of the gas specimen mixture at standard temperature and pressure. The density of the gas specimen mixture may be the real density of the gas specimen mixture based on the measured pressure and temperature, and the calculated heating value is the volume-based heating value of the gas specimen mixture at the measured temperature and pressure. In another embodiment, the processing subsystem is further configured to calculate the energy flow of the gas specimen mixture from the volume-based heating value of the gas specimen mixture at the measured temperature and pressure and volumetric flow rate of the gas specimen mixture. The volumetric flow rate of the gas specimen mixture may be measured by a flow meter. Calculating the energy flow of the gas specimen mixture includes multiplying the volume-based heating value of the gas specimen mixture at the measured temperature and pressure times the volumetric flow rate.

In a further embodiment, the processing subsystem is further configured to determine the mass flow rate of the gas specimen mixture by the steps including measuring the volumetric flow rate of the gas specimen mixture, determining the density of the gas specimen mixture, and calculating the mass flow of the gas specimen mixture based on the density and the volumetric flow rate. The volumetric flow rate may be measured by a flow meter. In one configuration, determining the density includes the steps including measuring the temperature and pressure of the gas specimen mixture, and calculating the density of the gas specimen mixture from the measured temperature and pressure. In another configuration, determining the density includes the steps including calculating the specific gravity of the gas specimen mixture from the molecular weight of the gas specimen mixture, and converting the calculated specific gravity to density using the measured inert component concentrations. Calculating the mass flow rate includes multiplying the density times the volumetric flow rate.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
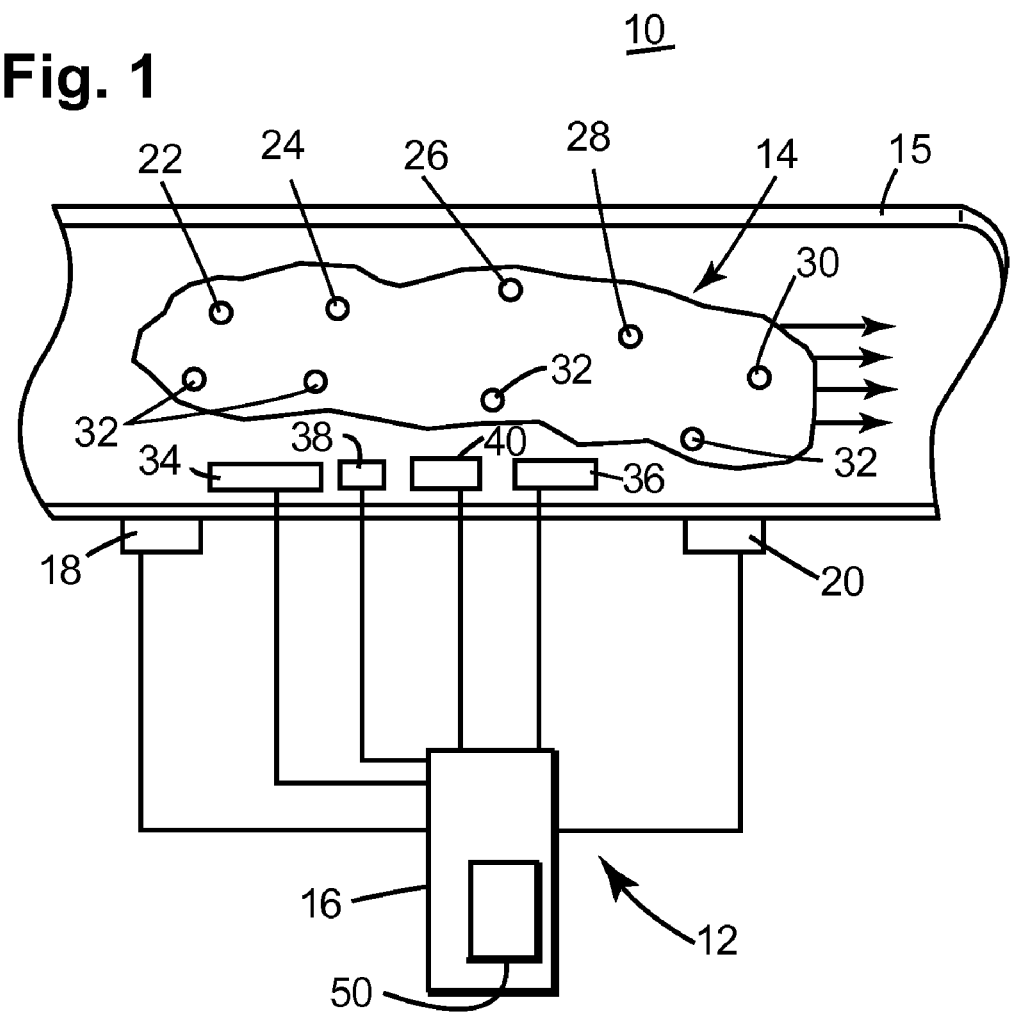
FIG. 1 is a cross-sectional schematic side view of one example of a gas specimen mixture analysis system in accordance with the present invention.

Aside from the embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In the field of gas analysis, if the properties of a gas flowing through a pipeline could be determined more precisely, gas could be transferred on the basis of quality rather than quantity, among other benefits. In order to make improvements in accuracy, however, there needs to be a way to better establish the totality of the gas mixture in the pipeline in the first instance. The subject invention provides an improved alternative to conventional systems.

In one embodiment of the subject invention, gas specimen mixture analysis system 10 includes subsystem 12 for measuring the speed of sound in gas specimen mixture 14. In one configuration, subsystem 12 includes a meter 16 (such as an ultrasonic flowmeter) including at least one transducer 18, or a pair of transducers 18 and 20, which are typically ultrasonic transducers. Any of a number of commercially available GE® ultrasonic flowmeters may be utilized, although the invention is not so limited.

Although gas specimen mixture 14 may be any multi-component gas flowing through pipe or conduit 15, in one example gas specimen mixture 14 is a multi-component gas such as natural gas, e.g. a hydrocarbon dominated gas, including inert or zero energy content components such as nitrogen 22 and carbon dioxide 24, as well as hydrocarbon components such as methane 26, ethane 28, propane 30, and heavier hydrocarbons 32 such as butane, pentane and the like, with each of components 22-32 within gas specimen mixture 14 in varying proportions. As used herein, "inert" components or gases refer to components or gases which have no energy content.

Gas specimen mixture analysis system 10 further includes nitrogen sensor 34 for measuring the concentration of nitrogen gas 22 in gas mixture 14, and carbon dioxide sensor 36 for measuring the concentration of carbon dioxide 24 in gas specimen mixture 14. Temperature sensor 38 measures the temperature of gas specimen mixture 14, and pressure sensor 40 measures the pressure. Nitrogen sensor 34, carbon dioxide sensor 36, temperature sensor 38, and pressure sensor 40 may be any of the various types of such sensors commercially available and known to those skilled in the art. If the inert or zero energy components were components other than nitrogen and carbon dioxide, appropriate sensors could be used, and nitrogen and carbon dioxide sensors are not necessary limitations of the invention. Also, insofar as specific embodiments or examples of the subject invention describe nitrogen and carbon dioxide as the inert or zero energy level components of a gas specimen mixture to be measured or analyzed, this is not a necessary limitation of the invention, and the methods and systems of the subject invention apply to any inert components.

Gas analysis system 10 further includes processing subsystem 50 which is responsive to the inert or zero energy content sensors, e.g. to nitrogen gas sensor 34 and carbon dioxide sensor 36, and is also responsive to temperature sensor 38, pressure sensor 40, and subsystem 12. As shown, processing subsystem 50 is included within meter 16, e.g. embedded in software in meter 16 which may be an ultrasonic flow meter. This is not a limitation of the invention, however. Processing subsystem 50 and associated methods may be part of an energy meter or other instrument, embedded in software therein or otherwise included therein as may be known to those skilled in the art, or may be part of a computer or other processor which may be separate from the remaining systems. These examples are not meant to be limiting, and all or part of the present invention may be implemented in a computer such as a digital computer, and/or incorporated in software module(s) and/or computer programs compatible with and/or embedded in conventional ultrasonic flow meters or energy meters, such software module(s) in one example for e.g. gathering data from the various sensors and generating the samples and making the computations and the like as described herein, and the computer's or meter's main components may include e.g.: a processor or central processing unit (CPU), at least one input/output (I/O) device (such as a keyboard, a mouse, a compact disk (CD) drive, and the like), a controller, a display device, a storage device capable of reading and/or writing computer readable code, and a memory, all of which are interconnected, e.g., by a communications network or a bus. The processing subsystems and methods of the present invention can be implemented as a computer and/or software program(s) stored on a computer readable medium in the computer or meter and/or on a computer readable medium such as a tape or compact disk. The processing subsystems and methods of the present invention can also be implemented in various meters or a plurality of computers, with the components residing in close physical proximity or distributed over a large geographic region and connected by a communications network, for example.

Processing subsystem 50 is configured in accordance with one embodiment of a method of the subject invention, namely, to establish the molecular weight of a gas specimen mixture flowing through a pipe or conduit, such as a hydrocarbon gas, e.g., natural gas. Thus, processing subsystem 50 is configured to generate a number of sample gas mixtures with varying percentages of hydrocarbon gases, step 60, FIG. 2. In one example, a list of 2904 hydrocarbon sample gas mixtures is generated with gas compositions as shown in Table 1.

TABLE 1

| Methane(C1) | Bal. |
|---|---|
| Ethane(C2) | 11 points over 0-10% |
| Propane(C3) | 11 points over 0-4% |
| Butane(C4) | 6 points over 0-1% |
| n-Pentane(C5) | 2 points over 0-0.3% |
| n-Hexane(C6) | 2 points over 0-0.2% |
| n-Heptane(C7) | 0 |
| n-Octane(C8) | 0 |
| n-Nonane(C9) | 0 |
| n-Decane(C10) | 0 |

The list is based on the Normal Range from AGA (American Gas Association) Report No. 8, which is incorporated herein by reference, but with two simplifications: (1) C6+ group is replaced by a single C6 composition, and (2) isomers are replaced by corresponding single-chain paraffin. The error of +/−0.04% found due to (1), and the error of +/−0.004% found due to (2) were both within acceptable limits.

Each sample gas mixture includes the measured inert gas components concentrations, in this example nitrogen gas and carbon dioxide concentrations, as measured by nitrogen sensor 34, FIG. 1, and carbon dioxide sensor 36. The pressure and the temperature are measured by, e.g. temperature sensor 38, FIG. 1, and pressure sensor 40. For each generated sample gas mixture, processing subsystem 50 calculates the speed of sound therein based on the measured pressure and temperature and the particular percentages of hydrocarbon gases therein, step 62, FIG. 2. The speed of sound is a thermodynamic gas property which depends on a gas' pressure and temperature, in this case the pressure and temperature of the gas specimen mixture in a pipe. In general, speed of sound (SS) can be expressed as a function of the composition of the gas specimen mixture, pressure (P) and temperature (T):

$$SS = F(\text{composition of gas specimen mixture}, P, T) \quad (1)$$

In natural gases, the dominant hydrocarbons are long-chain paraffins ($C_nH_{2n+2}$) as shown for example in Table 2 below, compiled from data for 394 GE gas turbine engines, showing normal range and expended range for gas turbine application, and normal range for custody transfer application from the aforementioned AGA Report No. 8. Except for methane, all ranges are from 0% to the percentage indicated.

TABLE 2

|  | Normal Range for Gas Turbine App. (from 95% of 394 turbine data) | Expended Range for Gas Turbine App. (from 99% of 394 turbine data) | Normal Range from AGA8 |
|---|---|---|---|
| Methane | 80%~100% | 60% | >45% |
| Ethane | 85% | 15% | <10% |
| Propane | 3% | 5% | <4% |
| Butane | 1% | 2% | <1% |
| Pentane | 0.3% | 0.6% | <0.3% |
| Hextane | 0.2% | 0.4% | C6+ total <0.2% |
| Heptane | 0.16% | 0.32% | C6+ total <0.2% |
| Octane | 0.02% | 0.04% | C6+ total <0.2% |
| Nonane | 0.01% | 0.025% | C6+ total <0.2% |
| Decane | 0.002% | 0.008% | C6+ total <0.2% |
| C11~20 tot. | 0.001% | 0.006% | 0 |
| $N_2$ | 5% | 31% | 50% |
| $CO_2$ | 4.5% | 31% | 30% |
| CO | 0% | 0.02% | 3% |
| $H_2O$ | 0.01% | 0.01% | 0.05% |
| Hydrogen | 0.02% | 0.2% | 10% |
| Helium | 0.02% | 0.06% | 0.20% |
| Argon | 0.002% | 0.05% | 0 |
| Oxgyen | 0.04% | 0.5% | 0 |
| $H_2S$ | 0% | 0.01% | 0.02% |

Because the dominant hydrocarbons are long-chain paraffins, equation (1) can be simplified to:

$$SS = F(MW_{CH}, \text{inert components}, P, T) \quad (2a)$$

or if nitrogen and carbon dioxide constitute a majority of the inert or zero energy content components, equation (1) can be simplified to:

$$SS = F(MW_{CH}, N_2\%, CO_2\%, P, T) \quad (2b)$$

where $MW_{CH}$ is the molecular weight for equivalent pure hydrocarbons of the gas specimen mixture flowing through a pipe, and $N_2\%$ and $CO_2\%$ are mole fractions (percentages) of nitrogen and carbon dioxide for the gas specimen mixture.

Figure 2:
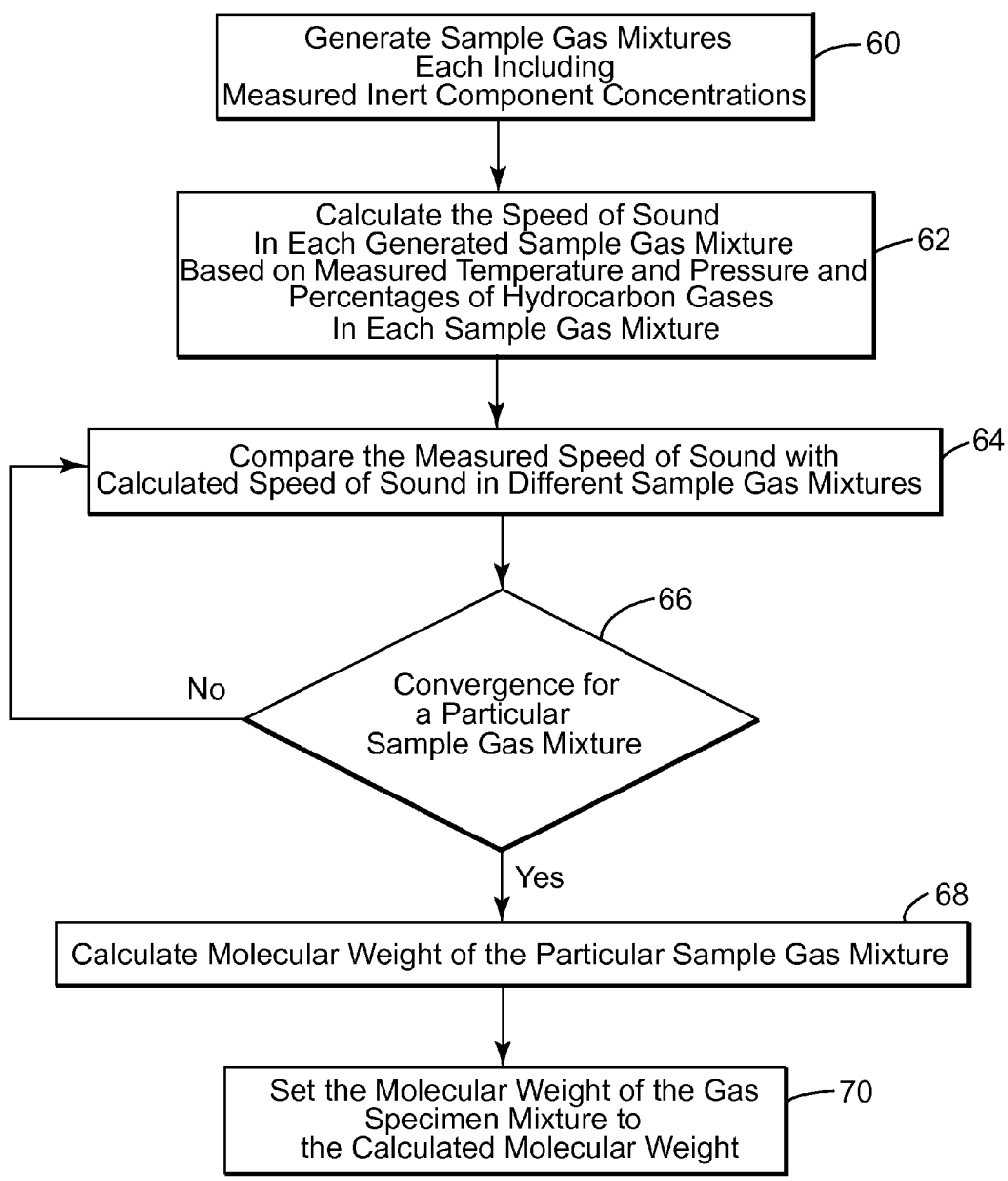
FIG. 2 is a flow chart depicting the primary steps of one example of a configuration of a processing subsystem and an associated method for analyzing a gas specimen mixture in accordance with the present invention.

After the speed of sound has been calculated for each generated sample gas mixture, processing subsystem 50 iteratively compares the measured speed of sound with the calculated speed of sound in different generated sample gas mixtures, step 64, FIG. 2 until convergence for a particular sample gas mixture, step 66. In one example, processing system 50 compares the measured speed of sound with the calculated speed of sound of the sample gas mixture containing 80% methane, 8% ethane, 3% propane, 1% butane, 0.3% pentane, and appropriate percentages of remaining components to total 100%. See Table 1. If the measured speed of sound in the gas specimen mixture does not converge with, the calculated speed of sound for that particular sample gas mixture, then a different sample gas mixture is selected, e.g. a sample gas mixture containing 81% methane, 7% ethane, 3% propane, 1% butane, 0.3% pentane, and appropriate percentages of remaining components to total 100%. If there is convergence between a particular sample gas mixture and the measured speed of sound, processing subsystem 50 then calculates the molecular weight of the particular sample gas mixture, step 68, and sets the molecular weight of the gas specimen mixture to the calculated molecular weight, step 70. Convergence may be set to equality between the measured and calculated speeds of sound, but in one variation, convergence is set to a difference between the measured speed of sound (in the gas specimen mixture) and the calculated speed of sound (in a particular sample gas mixture) of less than or equal to 0.001%.

The molecular weight of the particular sample gas mixture is calculated using the measured speed of sound in the gas specimen mixture using equation (2b), where for example, nitrogen and carbon dioxide are the major inert gas components. The step of setting the molecular weight of the gas specimen mixture to the calculated molecular weight thus provides the molecular weight of the gas specimen mixture to greater precision due to the iterative and dynamic nature of the subject invention. The "feedback" loop iteration using the generated sample gas mixtures, with only small incremental differences of concentrations of hydrocarbon gases therebetween, provides for a finer "tuning", and much greater accuracy is the result.

Figure 3:
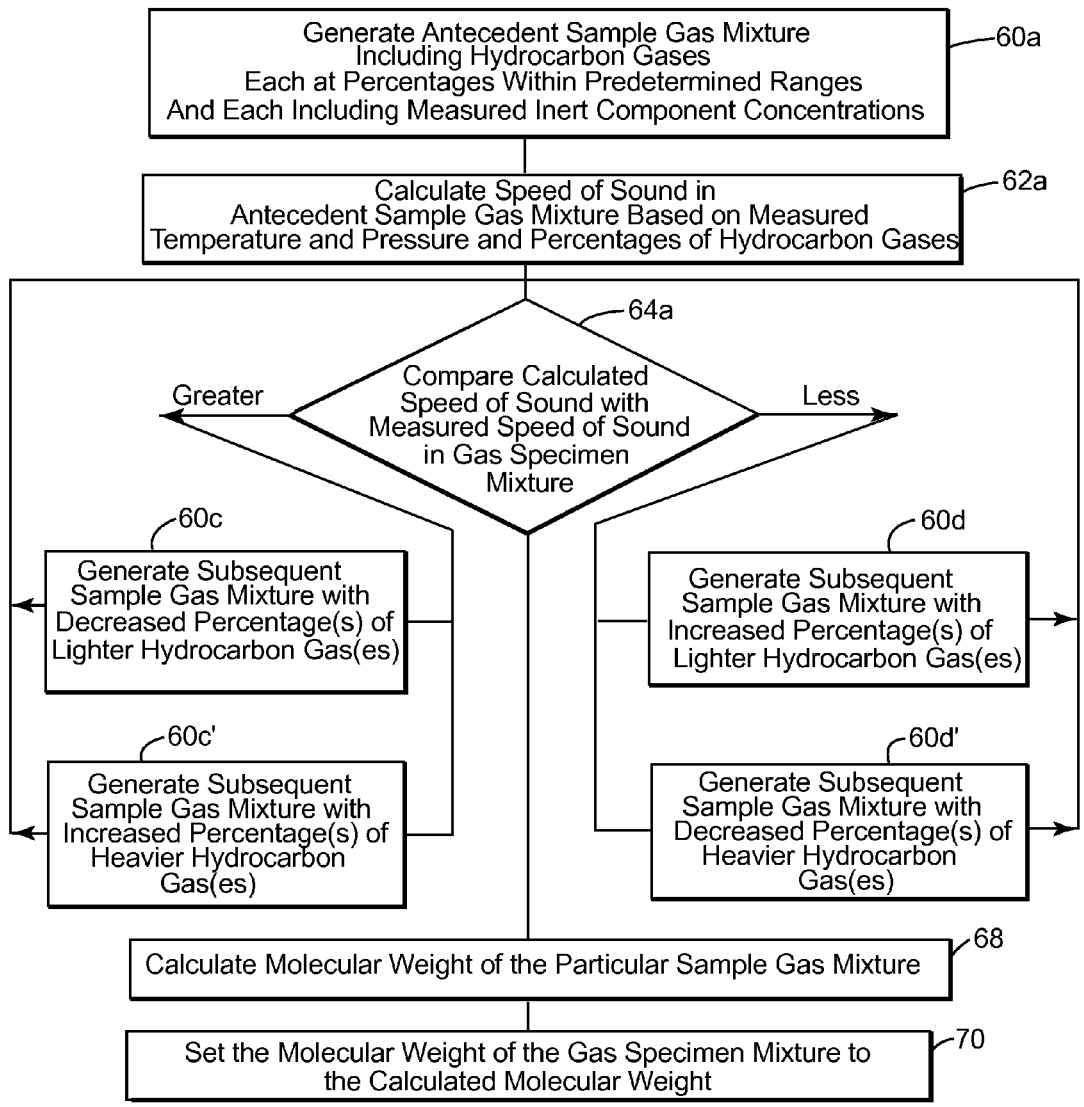
FIG. 3 is a flow chart depicting examples of additional steps for the processing subsystem and method of FIG. 2.

In one configuration, as part of generating a number of sample gas mixtures including measured inert components, such as nitrogen gas and carbon dioxide concentration, step 60, processing subsystem 50, FIG. 1 generates an antecedent sample gas mixture including hydrocarbon gases each at percentages which fall within a predetermined range, step 60a, FIG. 3. Again referring to Table 1, in one example, the predetermined range for methane is between 80%-100%; for ethane between 0%-8%; for propane between 0%-3%, and so on for the remaining components.

The goal is convergence, in order to calculate the molecular weight of the particular gas sample mixture and thus set the molecular weight of the gas specimen mixture in the conduit to the calculated molecular weight. Therefore, another particular example of the iterative process is as follows. The antecedent sample gas mixture is generated as described, and the speed of sound of the antecedent sample gas mixture is calculated, step 62a, FIG. 3 in the same ways as discussed with respect to step 62, FIG. 2, and compared with the measured speed of sound, step 64a, FIG. 3. When the calculated speed of sound in an antecedent sample gas mixture is greater than the measured speed of sound in the gas specimen mixture in the pipe, the calculated speed of sound must be reduced to lead to convergence due to the relationship of speed of sound and molecular weight. Thus, processing subsystem 50 may generate a subsequent sample gas mixture with percentages of lighter hydrocarbon gases decreased from the percentages of lighter hydrocarbon gases in the antecedent sample gas mixture, step 60c, FIG. 3. As noted, at least one hydrocarbon gas in the subsequent sample gas mixture is at a different percentage than in the antecedent sample gas, although more than one hydrocarbon gas percentage may be different than in the antecedent sample gas mixture. For example, if the concentration of methane in the antecedent sample gas mixture is 90% (see e.g. Table 1) and the calculated speed of sound must be reduced, the methane percentage in the subsequent sample gas mixture may be decreased to 80%. Alternatively to reduce the calculated speed of sound, processing subsystem 50 may generate a subsequent sample gas mixture with percentages of heavier hydrocarbon gases increased from percentages of heavier hydrocarbon gases in the antecedent sample gas mixture, step 60c'. For example, the percentage of nonane (a heavier hydrocarbon gas) in the subsequently generated sample gas mixture may be increased.

Conversely, when the calculated speed of sound in an antecedent sample gas mixture is less than the measured speed of sound in the gas specimen mixture, the calculated speed of sound must be increased to lead to convergence. Thus, processing subsystem 50 may generate a subsequent sample gas mixture with percentages of lighter hydrocarbon gases (e.g. methane, ethane) increased from the percentages of lighter hydrocarbon gases in the antecedent sample gas mixture, step 60d, FIG. 3. Again, at least one hydrocarbon gas in the subsequent sample gas mixture is at a different percentage than in the antecedent sample gas, although more than one hydrocarbon gas percentage may be different than in the antecedent sample gas mixture. Alternatively to achieve the same end, processing subsystem 50 may generate a subsequent sample gas mixture with percentages of heavier hydrocarbon gases (e.g. nonane, decane) decreased from percentages of heavier hydrocarbon gases in the antecedent sample gas mixture, step 60d'. Any combination of percentages of hydrocarbon gases, including increasing and decreasing respective lighter and heavier hydrocarbon gases in antecedent and subsequent sample gas mixtures, may be used. Also, as noted above, if the calculated speed of sound for the generated antecedent sample gas mixture is equal to the measured speed of sound, or the difference is less than or equal to e.g. 0.001%, there would be no need to generate a subsequent sample gas mixture, and the molecular weight could be calculated directly, step 68.

The result is a more accurate evaluation of the quality of the analyzed gas specimen mixture flowing in the pipe, by virtue of the iterative incremental dynamic process of the subject invention, which leads to an accurate assessment of molecular weight of the gas specimen mixture, and thus to more accurate determinations of gas properties such as heating value, mass flow, and energy flow, which are discussed in more detail below.

Figure 4:
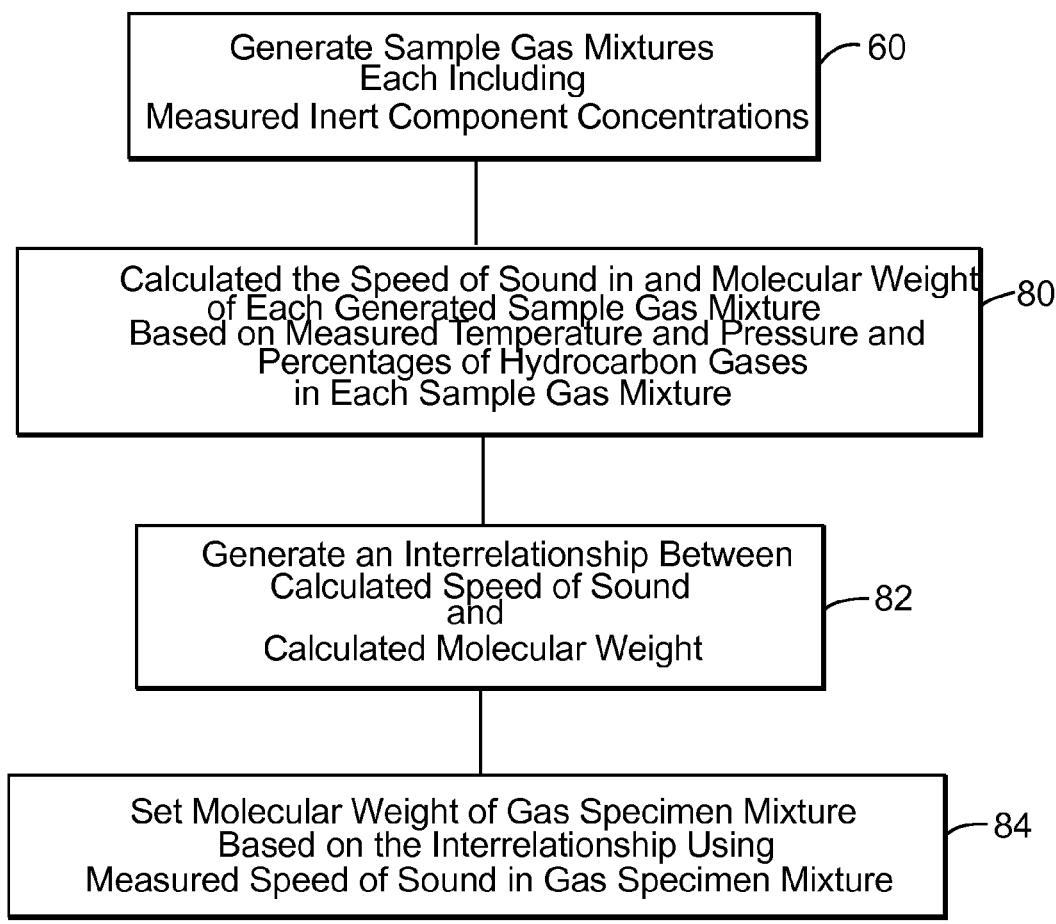
FIG. 4 is a flow chart depicting the primary steps of a further example of a configuration of the processing subsystem and an associated method for analyzing a gas specimen mixture in accordance with the present invention.

In another embodiment of the subject invention, gas specimen mixture analysis system 10, FIG. 1 includes the features described above including the features of processing subsystem 50, and operates in a similar manner as described above, except that instead of iteratively comparing the measured speed of sound with the calculated speed of sound in different gas mixtures until convergence for a particular gas mixture, calculating the molecular weight, and setting the molecular weight of the gas specimen mixture to the calculated molecular weight (as shown e.g. in steps 64-70 in FIG. 2), processing subsystem 50 is configured as shown in FIG. 4.

Figure 5:
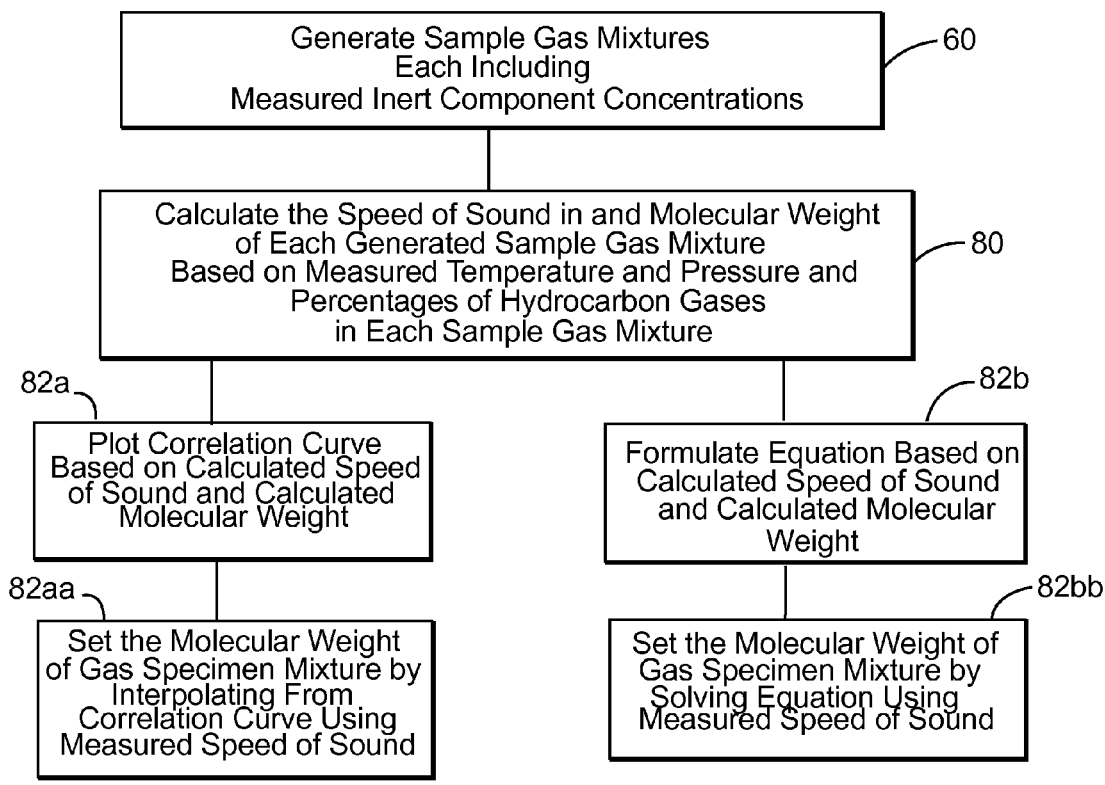
FIG. 5 is a flow chart depicting examples of additional steps for the processing subsystem and method of FIG. 4.
Figure 6:
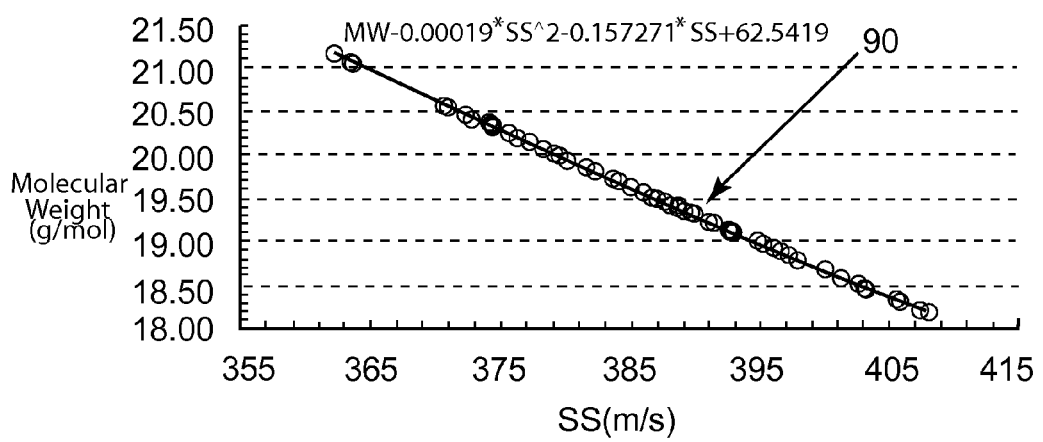
FIG. 6 is a plot of calculated molecular weight and speed of sound in one example showing how the molecular weight of a gas specimen mixture may be set in accordance with the present invention.

Processing subsystem 50 of the embodiment of FIG. 4 is configured in accordance with another embodiment of a method of the subject invention, where after generating a number of sample gas mixtures, step 60, processing subsystem 50 not only calculates the speed of sound in each generated sample gas mixture based on the measured pressure and temperature (of the gas specimen mixture flowing in the pipe) and the particular percentages of hydrocarbon gases therein, but also calculates the molecular weight, step 80. Processing subsystem 50 is further configured to generate an interrelationship between the calculated speed of sound and molecular weight for each generated sample gas mixture, step 82, and using the measured speed of sound in the gas specimen mixture, sets the molecular weight of the gas specimen mixture based on the interrelationship between the calculated speed of sound and molecular weight for the generated sample gas mixture, step 84. In one variation, generating an interrelationship includes plotting a correlation curve based on the calculated speed of sound and calculated molecular weight for each generated sample gas mixture, step 82a, FIG. 5. A sample correlation curve 90 is shown in FIG. 6. Speed of sound is plotted on the x-axis, and molecular weight is plotted on the y-axis. In this case, the molecular weight of the gas specimen mixture is set based by interpolating from correlation curve 90 using the measured speed of sound in the gas specimen mixture, step 82aa, FIG. 5. For example, if the measured speed of sound is 385 m/s, the molecular weight can be interpolated from correlation curve 90, FIG. 6, as 19.70 g/mol.

In the example of FIG. 6, correlation curve 90 between speed of sound and molecular weight is for sample gas mixtures at 25° C. and 602 psia with 5% nitrogen concentration and 2% carbon dioxide concentration, with each data point representing one sample gas mixture. FIG. 6 further shows that speed of sound correlates to molecular weight very well, regardless of large variations in the hydrocarbon compositions among sample gas mixtures. Once the inert content in the gas specimen mixture in a conduit is known, e.g. the nitrogen and carbon dioxide concentrations, speed of sound is only a function of the molecular weight of the gas specimen mixture at a given temperature and pressure. Correlation curve 90 of FIG. 6 represents a list of seventy-two (72) generated sample gas mixtures, based on the Normal Range compiled from gas data from 394 GE Gas Turbines, and the list of generated sample gas mixtures were generated with the gas compositions as shown in Table 3.

TABLE 3

| Methane(C1) | Bal. | | |
|---|---|---|---|
| Erhane(C2) | 2% | 4% | 10% |
| Propane(C3) | 1% | 2% | 5% |
| Butane(C4) | 0.5% | 2% | |
| n-Pentane(C5) | 0.1% | 0.3% | |
| n-Hexane(C6) | 0.04% | 0.16% | |
| n-Heptane(C7) | 0.04% | 0.16% | |
| n-Octane(C8) | 0.005% | 0.025% | |
| n-Nonane(C9) | 0.002% | 0.006% | |
| n-Decane(C10) | 0.001% | 0.002% | |
| N2 | 5% | | |
| CO2 | 2% | | |
| P (psia) | 15 psia | 308 psia | 602 psia |
| T (° C.) | 0° C. | 25° C. | 50° C. |

In this example, the seventy-two (72) sample gas mixtures are created by full factorial of C2~C6 (3×3×2×2×2), with various combinations of C7~C10, and C1 as the balance, and nitrogen and carbon dioxide concentrations fixed at 5% and 2% respectively. For each generated gas sample mixture, its speed of sound (SS), gas density ($\rho$), compressibility factor (Z), specific heat at constant pressure (Cp), specific heat at constant volume (Cv), and isentropic ratio ($\kappa$) are calculated for pressures at 15, 308 and 602 psia, and for temperature at 0°, 25° and 50° C., respectively, utilizing commercial SonicWare software by Lomic, Inc., which uses Detailed Characterization Methods published in AGA (American Gas Association) Report No. 10 and Report No. 8, each of which is incorporated herein by reference. All uncertainties were found to be well within acceptable limits. Uncertainties due to curve fit, for example, were found to be mostly within 0.05%. Errors due to variations in gas composition, for example, were found to be within +/−0.03% for twenty-five gas samples. At various pressures and temperatures, correlation curves of speed of sound and molecular weight all consistently demonstrated good correlation.

In another variation, generating an interrelationship includes formulating an equation based on the calculated speed of sound and molecular weight for each generated sample gas mixture, step 82b, and setting the molecular weight of the gas specimen mixture by solving the equation using the measured speed of sound in the gas specimen mixture, step 82bb. One equation reflecting the interrelationship is:

$$MW = 0.000119 \cdot SS^2 - 0.157271 \cdot SS + 62.5419 \quad (3)$$

Also as shown in FIG. 6, where the variable MW is the molecular weight of the sample gas mixture in grams per mole and the variable SS is the speed of sound of the sample gas mixture in meters per second, at 25° C., 602 psia for 5% nitrogen concentration and 2% $CO_2$ concentration. Also, in the various embodiments of the gas analysis system and method of the subject invention, the hydrocarbon gases in the sample gas mixtures include some combination of methane, ethane, propane, butane, pentane, hexane, heptane, octane, nonane, and decane, as well as other hydrocarbon gases which also may be included in the combination.

The gas specimen analysis systems and methods of the present invention also may include—in addition to determining the molecular weight of the gas specimen mixture flowing through a pipe—determining the heating value of the gas specimen mixture and/or the energy flow of the gas specimen mixture, and/or the mass flow rate of the gas specimen mixture. Typically, these determinations will be made utilizing the molecular weight as determined in accordance with the present invention for better accuracy.

Figure 7:
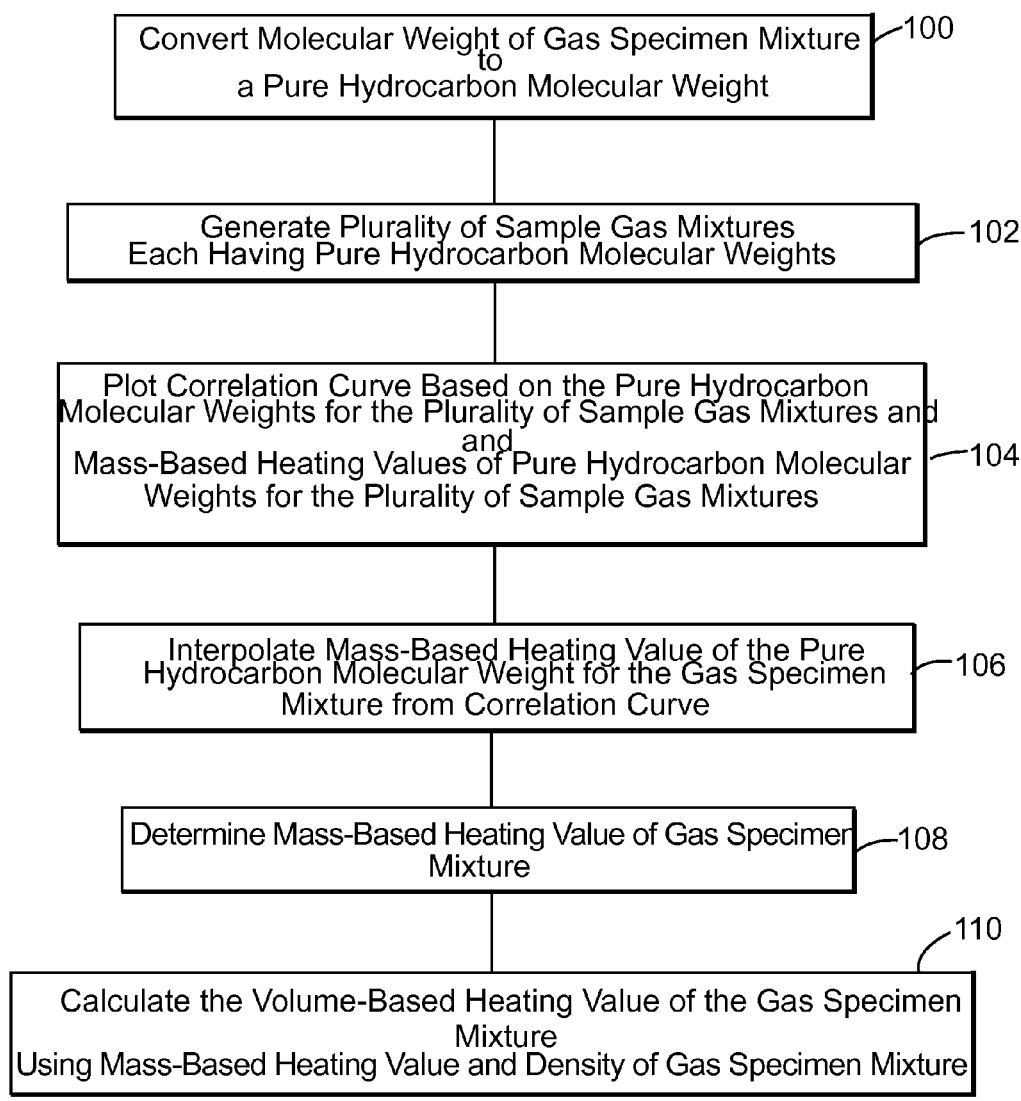
FIG. 7 is a flow chart depicting the primary steps of one example of a configuration of the processing subsystem and an associated method for analyzing a gas specimen mixture including calculating the heating value in accordance with the present invention.

Processing subsystem 50, FIG. 1 is configured in accordance with an embodiment of another method of the subject invention to determine the heating value of the gas specimen mixture flowing through a pipe. In this embodiment processing subsystem 50 determines the heating value by converting the molecular weight of the gas specimen mixture to a pure, or corresponding, hydrocarbon molecular weight, step 100, FIG. 7. and generating a plurality of sample gas mixtures each having pure hydrocarbon molecular weights, step 102, with varying percentages of different hydrocarbon gases within a predetermined range. Typically these sample gas mixtures are generated in a similar manner to the other sample gas mixtures discussed herein, but in this case the sample gas mixtures are generated without the measured inert content concentrations, such as measured nitrogen and carbon dioxide concentrations, as discussed more fully below. Next, a correlation curve is plotted based on the pure hydrocarbon molecular weights for the plurality of sample gas mixtures and mass-based heating values of the pure hydrocarbon molecular weights for the plurality of sample gas mixtures, step 104. The mass-based heating values of the pure hydrocarbon molecular weights for the generated sample gas mixtures are obtained by the correlation curve, i.e. the mass-based heating value of the pure hydrocarbon molecular weight for the gas specimen mixture can be interpolated from the correlation curve, step 106. As discussed further below, the mass-based heating value for the gas specimen mixture is determined, step 108, and the volume-based heating value of the gas specimen mixture is calculated using the mass-based heating value of the gas specimen mixture and the density of the gas specimen mixture, step 1110.

Figure 8:
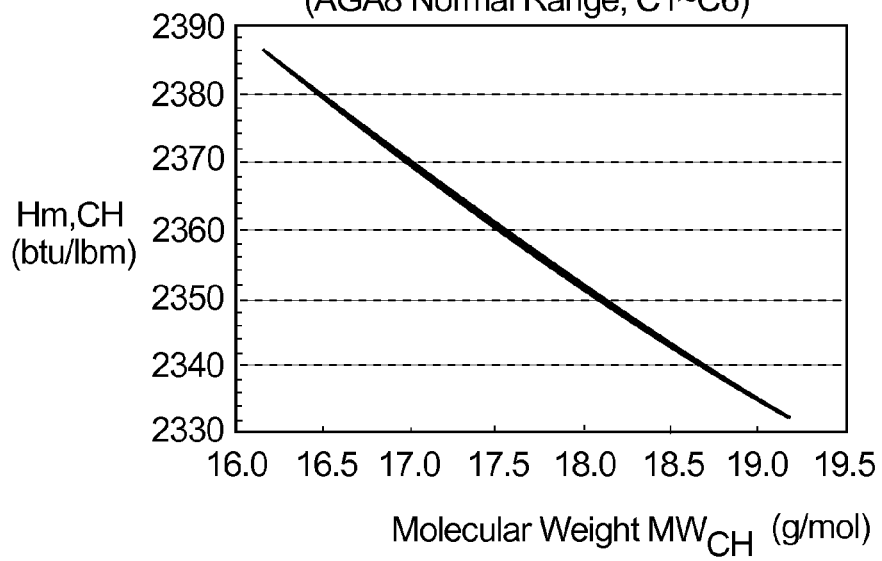
FIG. 8 is one example of a plot of molecular weight and mass-based heating value for a number of generated pure hydrocarbon sample gas mixtures.

The mass-based heating value correlation curve is shown in FIG. 8. It is a chemical property correlation between mass-based heating values, $H_{m,CH}$(BTU/lbm, gross or net), and molecular weight ($MW_{CH}$) for various hydrocarbon compositions within the Normal Range from AGA Report No. 8, discussed above. It is a chemical property only related to gas compositions, and independent of process pressure and temperature conditions. The correlation curve of FIG. 8 is based on a list of 2904 generated sample gas mixtures, as discussed above with regard to Table 1. Some uncertainties in $H_{m,CH}$ are introduced by variations in gas compositions which have the same molecular weight, with the largest uncertainty arising from the curve's mid-region. Even in such a case, the uncertainty was found to be +/−0.032% at $MW_{CH}$=17.655, which is within acceptable limits. For a group of twenty-five sample gas mixtures, the uncertainties in $H_m$ (net) due to changes in hydrocarbon compositions was found to be within +/−0.04%, which is within an acceptable limit.

As discussed above, in one variation, the molecular weight of the gas specimen mixture is converted to a pure, or corresponding, hydrocarbon molecular weight, step 100, by replacing the measured inert concentrations—nitrogen and carbon dioxide concentrations in one example—with proportionately equivalent concentrations of hydrocarbon gases. The molecular weight of pure, or corresponding, hydrocarbons $MW_{CH}$ can be calculated from the molecular weight of the gas specimen mixture MW (as determined according to the system and methods of the present invention for increased accuracy) using equation (4) with the measured nitrogen and carbon dioxide concentrations:

$$MW_{CH} = \frac{MW - MW_{N_2} \cdot N_2\% - MW_{CO_2} \cdot CO_2\%}{1 - N_2\% - CO_2\%} \quad (4)$$

Once $MW_{CH}$ is found, the corresponding mass-based heating value (gross or net) for hydrocarbons, $H_{m,CH}$ can be found from the curve of FIG. 8 by interpolation, i.e. step 106 above. After the heating value is interpolated, it is the heating value for a pure amount of hydrocarbon gases. The amount of nitrogen and carbon dioxide concentrations must then be taken into account by, conversely, replacing the pure amount of hydrocarbon gases with these values.

Thus, $H_{m,CH}$ is converted to mass-based heating value with nitrogen and carbon dioxide concentrations included, i.e. $H_m$ is determined by equation (5):

$$H_m = H_{m,CH} \cdot \frac{MW - MW_{N_2} \cdot N_2\% - MW_{CO_2} \cdot CO_2\%}{MW} \quad (5)$$

Thus, the step of determining the heating value of the gas specimen mixture, step 108, is achieved by replacing the proportionately equivalent concentrations of hydrocarbon gases with the measured nitrogen gas and carbon dioxide concentrations. The mass-based heating value is therefore known, and the heating value of the gas specimen mixture can be calculated by multiplying the mass-based heating value of the gas specimen mixture times the density of the gas specimen mixture, step 110, using equation (6):

$$H_v = H_m \cdot \rho \quad (6)$$

If the heating value at standard temperature and pressure is the desired quantity, then the density of the gas specimen mixture is a standard density, $\rho_0$, for the gas specimen mixture based on predetermined temperature and pressure values. In one example, standard temperature and pressure are 60° F. and 14.73 psia. Alternatively, the heating value at the measured temperature and pressure may be calculated, step 110, based on the measured temperature and pressure, if the heating value at the actual measured temperature and pressure is desired. It can be seen that because heating value is determined ultimately from the molecular weight of the gas specimen mixture, which is found in accordance with the inventive methods described above, a more precise heating value is obtained for the analyzed gas.

Figure 9:
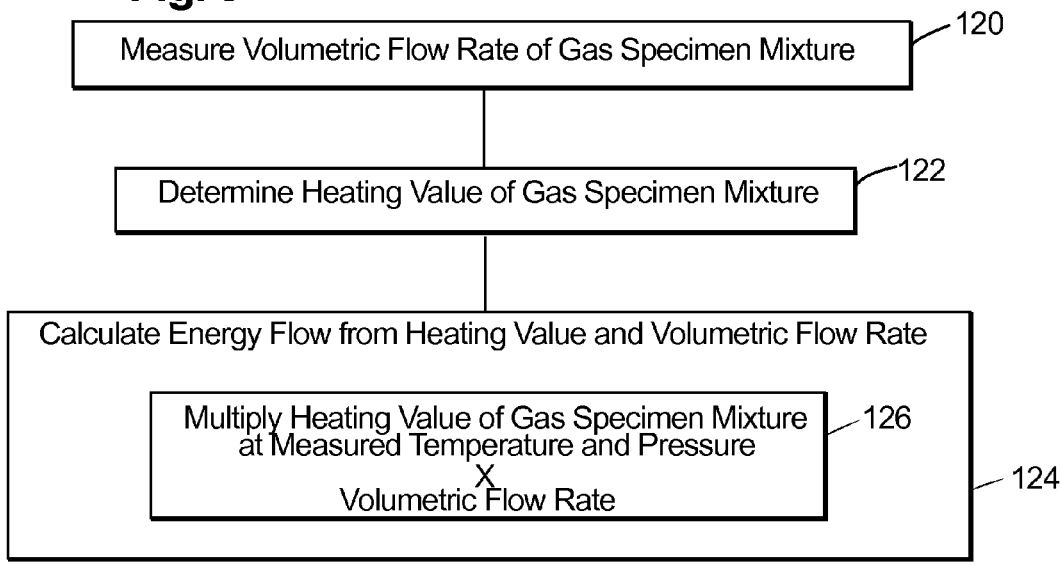
FIG. 9 is a flow chart depicting the primary steps of one example of a configuration of the processing subsystem and an associated method for analyzing a gas specimen mixture including calculating the energy flow in accordance with the present invention.

In a further embodiment, processing subsystem 50, FIG. 1 is configured in accordance with an embodiment of another method of the subject invention, to calculate the energy flow of a gas specimen mixture flowing through the conduit. In this embodiment processing subsystem 50 calculates the energy flow from the volume-based heating value of the gas specimen mixture at the measured temperature and pressure, and the volumetric flow rate of the gas specimen mixture. The volumetric flow rate of the gas specimen mixture in the pipe 15, FIG. 1 is measured by meter 16 such as an ultrasonic flow meter, step 120, FIG. 9, and the volume-based heating value of the gas specimen mixture is determined, step 122, in one example by processing subsystem 50 so configured, including steps 100-110, FIG. 7 and as described above. Thus in this embodiment, the energy flow through the conduit is calculated from the volume-based heating value and the volumetric flow rate, step 124, FIG. 9 and one way of calculating the energy flow is by multiplying the volume-based heating value $H_v$ (BTU/cf) of the gas specimen mixture at the measured temperature and pressure times the volumetric flow rate Q (cf/sec), step 126. Thus, it can be seen that since energy flow is based on heating value, and heating value is determined in accordance with the invention, more precise energy flow information results.

Figure 10:
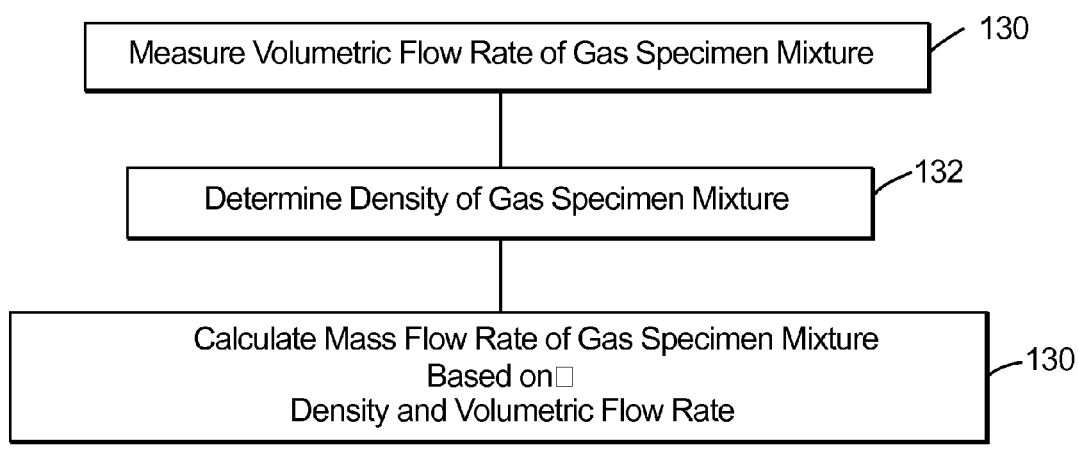
FIG. 10 is a flow chart depicting the primary steps of one example of a configuration of the processing subsystem and an associated method for analyzing a gas specimen mixture including calculating the mass flow rate in accordance with the present invention.

In still a further embodiment, processing subsystem 50, FIG. 1 is configured in accordance with another method of the invention, to determine the mass flow rate of the gas specimen mixture flowing through the conduit. In this embodiment processing subsystem 50 determines the mass flow rate by measuring the volumetric flow rate of the gas specimen mixture, step 130, FIG. 10, which can be measured by a flow meter, and determining the density of the gas specimen mixture, step 132. The density of the gas specimen mixture may be determined in at least one of two ways. A first way includes measuring the temperature and pressure of the gas specimen mixture, e.g. using temperature sensor 38 and pressure sensor 40, FIG. 1, and calculating the density from the measured temperature and pressure. A second way includes calculating the specific gravity of the gas specimen mixture from the molecular weight of the gas specimen mixture—e.g. the molecular weight determined by the methods and configuration of processing subsystem 50 as discussed herein—and using the Gross Characterization Method from AGA8, which is incorporated herein by reference, to calculate density. Once the density is determined the mass flow rate of the gas specimen mixture is calculated based on the density and volumetric flow rate, step 134, by multiplying the density times the volumetric flow rate e.g. by equation (7):

$$m = \rho \cdot Q \quad (7)$$

where m is mass flow rate, $\rho$ is density, and Q is volumetric flow rate measured by a flowmeter.

As noted, the values for density and specific gravity for use in determining energy flow and/or mass flow rate as set forth above may obtained in various ways. Standard density may be calculated at one atmosphere from the equation of state for ideal gas:

$$\rho_0 = \frac{P \cdot MW}{R \cdot T} \quad (8)$$

where $\rho_0$ is standard density, P=14.73 psia, T=60° F. and R=8.31 J/molK.

Standard density may also be calculated, more accurately, from a gas sample with molecular weight using AGA8 Detailed Characterization Method, which is incorporated herein by reference.

If real density is utilized in the determination of energy flow and/or mass flow rate, AGA Report No. 8 publishes a Gross Characterization Method, which is also incorporated herein by reference, for calculating natural (hydrocarbon) gas real density at a measured pressure and temperature, treating natural (hydrocarbon) gas as a mixture of three components: nitrogen, carbon dioxide and hydrocarbons. It uses a virial equation of state model, where compressibility, Z, is expanded as a series of molar density, with second and third virial coefficients. Virial coefficients are complex functions of composition and temperature. The Gross Characterization Method utilizes specific gravity, nitrogen and carbon dioxide mole fractions as inputs, and solves for compressibility (or density) in an iterative process. Specific gravity is the ratio of a gas' density to that of air at a specific pressure and temperature. If the specified pressure is one atmosphere, specific gravity is the ratio of molecular weight of the gas to that of air for an ideal gas.

Density at the measured pressure and temperature may also be calculated from a generated sample gas with the same molecular weight by the AGA8 Detailed Characterization Method as discussed herein, and which is incorporated herein by reference. In such a case, the density is determined by measuring the pressure and temperature of the gas specimen mixture in the conduit, and calculating the density of the particular sample gas mixture from the measured temperature and pressure. Then the density of the gas specimen mixture is set to the calculated density.

Figure 11:
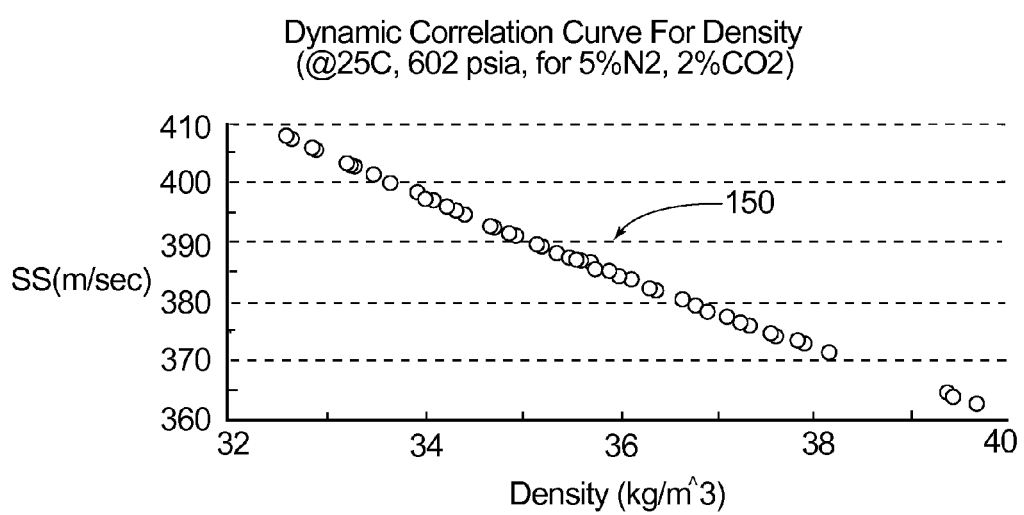
FIG. 11 is one example of a plot of speed of sound and density for a number of generated gas samples.

The real density of a gas specimen mixture in a pipe at measured temperature and pressure may also be determined by interpolating from a correlation curve. FIG. 11 shows an example of such a correlation curve 150 for density at 25° C., 602 psia, with 5% nitrogen concentration and 2% carbon dioxide concentration. It can be seen from FIG. 11 that if the speed of sound is measured, the real density may be determined using curve 150. FIG. 11 includes data for the seventy-two (72) sample gas mixtures of Table 1. In each of the calculations and determinations uncertainties arise, such as uncertainties in nitrogen, carbon dioxide, temperature and pressure measurements, and composition variations. In all instances, however, uncertainties were within acceptable limits, and improved accuracy was maintained. Moreover, the use of portions of AGA (American Gas Association) Report No. 8 and Report No. 10 are not necessary limitations of the invention, and other equivalent methodology may be used with the systems and methods of the present invention.

Accordingly, the various embodiments of the present invention provide more accurate analysis of the properties of a gas flowing through a pipe or conduit system, including a more precise determination of the molecular weight of the gas and information determined therefrom, and the analysis, measurements and determinations can be achieved in the field compatibly with existing instruments if desired.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed. Those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A system for analyzing a gas specimen mixture comprising:

at least one inert component sensor for measuring the concentrations of inert components in the gas specimen mixture;

a pressure sensor for measuring the pressure of the gas specimen mixture;

a temperature sensor for measuring the temperature of the gas specimen mixture;

a subsystem for measuring the speed of sound in the gas specimen mixture; and a processing subsystem, responsive to the at least one inert component sensor, the pressure sensor, the temperature sensor, and the subsystem for measuring the speed of sound, and configured to:

generate a number of sample gas mixtures with varying percentages of hydrocarbon gases but each including the measured inert component concentrations, calculate, for each generated sample gas mixture, the speed of sound therein based on the measured pressure and temperature and the particular percentages of hydrocarbon gases therein, iteratively compare the measured speed of sound with the calculated speed of sound in different sample gas mixtures until convergence for a particular sample gas mixture, calculate the molecular weight of the particular sample gas mixture, and set the molecular weight of the gas specimen mixture to the calculated molecular weight.

2. The system of claim 1 in which the at least one inert component sensor includes a nitrogen sensor for measuring the nitrogen gas concentration in the gas specimen mixture and a carbon dioxide sensor for measuring the concentration of carbon dioxide in the gas specimen mixture.

3. The system of claim 1 in which convergence is set to a difference between the measured speed of sound and a calculated speed of sound less than or equal to 0.001%.

4. The system of claim 1 in which the subsystem for measuring the speed of sound includes at least one ultrasonic transducer.

5. The system of claim 1 in which the processing subsystem is configured to generate an antecedent sample gas mixture including hydrocarbon gases each at percentages which fall within predetermined ranges.

6. The system of claim 5 in which the processing subsystem is configured to generate a subsequent sample gas mixture with at least one hydrocarbon gas at a different percentage than in the antecedent sample gas mixture but still constrained to fall within the predetermined range.

7. The system of claim 6 in which the processing subsystem, when the calculated speed of sound in an antecedent sample gas mixture is greater than the measured speed of sound in the gas specimen mixture, is configured to generate a subsequent sample gas mixture with percentages of lighter hydrocarbon gases decreased from the percentages of lighter hydrocarbon gases in the antecedent sample gas mixture.

8. The system of claim 7 in which the processing subsystem, when the calculated speed of sound in an antecedent sample gas mixture is greater than the measured speed of sound in the gas specimen mixture, is configured to generate a subsequent sample gas mixture with percentages of heavier hydrocarbon gases increased from the percentages of the heavier hydrocarbon gases in the antecedent sample gas mixture.

9. The system of claim 6 in which the processing subsystem, when the calculated speed of sound in an antecedent sample gas mixture is less than the measured speed of sound in the gas specimen mixture, is configured to generate a subsequent sample gas mixture with percentages of lighter hydrocarbon gases increased from the percentages of lighter hydrocarbon gases in the antecedent sample gas mixture.

10. The system of claim 9 in which the processing subsystem, when the calculated speed of sound in an antecedent sample gas mixture is less than the measured speed of sound in the gas specimen mixture, is configured to generate a subsequent sample gas mixture with percentages of heavier hydrocarbon gases decreased from the percentages of heavier hydrocarbon gases in the antecedent sample gas mixture.

11. The system of claim 1 in which the processing subsystem is further configured to determine the heating value of the gas specimen mixture by the steps comprising:
converting the molecular weight of the gas specimen mixture to a pure hydrocarbon molecular weight;
generating a plurality of sample gas mixtures each having pure hydrocarbon molecular weights;
plotting a correlation curve based on the pure hydrocarbon molecular weights for the plurality of sample gas mixtures and mass-based heating values of the pure hydrocarbon molecular weights for the plurality of sample gas mixtures;
interpolating the mass-based heating value of the pure hydrocarbon molecular weight for the gas specimen mixture from the correlation curve;
determining the mass-based heating value of the gas specimen mixture; and
calculating the volume-based heating value of the gas specimen mixture using the mass-based heating value of the gas specimen mixture and density of the gas specimen mixture.

12. The system of claim 11 in which converting the molecular weight of the gas specimen mixture to a pure hydrocarbon molecular weight includes replacing the measured inert component concentrations with proportionately equivalent concentrations of hydrocarbon gases.

13. The system of claim 12 in which determining the mass-based heating value of the gas specimen mixture includes replacing the proportionately equivalent concentrations of hydrocarbon gases with the measured inert component concentrations.

14. The system of claim 11 in which calculating the volume-based heating value of the gas specimen mixture includes multiplying the mass-based heating value of the gas specimen times the density of the gas specimen mixture.

15. The system of claim 14 in which the density of the gas specimen mixture is a standard density for the gas specimen mixture based on predetermined temperature and pressure values, and the calculated heating value is the volume-based heating value of the gas specimen mixture at standard temperature and pressure.

16. The system of claim 14 in which the density of the gas specimen mixture is the real density of the gas specimen mixture based on the measured pressure and temperature, and the calculated heating value is the volume-based heating value of the gas specimen mixture at the measured temperature and pressure.

17. The system of claim 16 in which the processing subsystem is further configured to calculate the energy flow of the gas specimen mixture from the volume-based heating value of the gas specimen mixture at the measured temperature and pressure and volumetric flow rate of the gas specimen mixture.

18. The system of claim 17 in which the volumetric flow rate of the gas specimen mixture is measured by a flow meter.

19. The system of claim 17 in which calculating the energy flow of the gas specimen mixture includes multiplying the volume-based heating value of the gas specimen mixture at the measured temperature and pressure times the volumetric flow rate.

20. The system of claim 1 in which the processing subsystem is further configured to determine the mass flow rate of the gas specimen mixture by the steps comprising:
measuring the volumetric flow rate of the gas specimen mixture;
determining the density of the gas specimen mixture; and
calculating the mass flow of the gas specimen mixture based on the density and the volumetric flow rate.

21. The system of claim 20 in which the volumetric flow rate is measured by a flow meter.

22. The system of claim 20 in which determining the density includes:
measuring the temperature and pressure of the gas specimen mixture;
calculating the density of the particular sample gas mixture from the measured temperature and pressure; and
setting the density of the gas specimen mixture to the calculated density.

23. The system of claim 20 in which determining the density includes:
calculating the specific gravity of the gas specimen mixture from the molecular weight of the gas specimen mixture, and converting the calculated specific gravity to density using the measured inert component concentrations.

24. The system of claim 20 in which calculating the mass flow rate includes multiplying the density times the volumetric flow rate.

* * * * *